(12) United States Patent
Rajh et al.

(10) Patent No.: US 6,677,606 B1
(45) Date of Patent: Jan. 13, 2004

(54) DOPA AND DOPAMINE MODIFICATION OF METAL OXIDE SEMICONDUCTORS, METHOD FOR ATTACHING BIOLOGICAL MOLECULES TO SEMICONDUCTORS

(75) Inventors: Tijana Rajh, Naperville, IL (US); Tatjana Paunesku, Woodridge, IL (US); Gayle E. Woloschak, Chicago, IL (US); Marion C. Thurnauer, Downers Grove, IL (US)

(73) Assignee: University of Chicago, Chicago, IL (US)

(*) Notice: Subject to any disclaimer, the term of this patent is extended or adjusted under 35 U.S.C. 154(b) by 431 days.

(21) Appl. No.: 09/606,429

(22) Filed: Jun. 28, 2000

(51) Int. Cl.[7] .................. H01L 35/24; H01L 51/00; H01L 29/24; H01L 21/44; H01S 1/00; H01S 3/00; G01N 23/00; G21K 7/00; G01J 1/58

(52) U.S. Cl. ................... 257/40; 250/251; 250/302; 250/307; 250/315.3; 250/328; 250/459.1; 257/102; 257/103; 438/677

(58) Field of Search .................. 250/251, 328, 250/315.3, 307, 302, 459.1; 438/677; 257/40, 102, 103, 228

(56) References Cited

U.S. PATENT DOCUMENTS

| | | | | |
|---|---|---|---|---|
| 4,885,633 A | * | 12/1989 | Buck | 348/135 |
| 5,302,832 A | * | 4/1994 | Kitagawara et al. | 250/459.1 |
| 5,506,420 A | * | 4/1996 | Kossovsky et al. | 257/40 |
| 5,591,578 A | * | 1/1997 | Meade et al. | 435/6 |
| 5,965,877 A | * | 10/1999 | Wood et al. | 250/227.15 |
| 5,990,479 A | * | 11/1999 | Weiss et al. | 250/307 |
| 6,043,428 A | * | 3/2000 | Han et al. | 136/263 |
| 6,051,194 A | * | 4/2000 | Peill et al. | 422/186 |
| 6,125,529 A | * | 10/2000 | Rosen et al. | 29/612 |
| 6,180,496 B1 | * | 1/2001 | Farrens et al. | 438/455 |
| 6,271,130 B1 | * | 8/2001 | Rajh et al. | 438/677 |
| 6,306,610 B1 | * | 10/2001 | Bawendi et al. | 435/7.1 |
| 6,331,262 B1 | * | 12/2001 | Haddon et al. | 252/502 |
| 6,414,318 B1 | * | 7/2002 | Uber et al. | 250/389 |
| 6,545,290 B2 | * | 4/2003 | Lorin et al. | 257/40 |

OTHER PUBLICATIONS

N. Serpone, et al. Subnanosecond Relaxation Dynamics . . . . *J. Phys. Chem.* 99, 16655 (1995).

* cited by examiner

Primary Examiner—John R. Lee
Assistant Examiner—Mary El-Shammaa
(74) Attorney, Agent, or Firm—Cherskov & Flaynik

(57) ABSTRACT

A method is provided for selective binding and detecting target molecules, and a method for detecting biological molecules, the method comprising supplying a semi-conductor capable of charge pair separation, and juxtaposing affinity moieties to the semi-conductor so as to effect changes in the charge pair separation characteristics when the affinity molecules are bound to the target molecules.

34 Claims, 5 Drawing Sheets

DOPA AND DOPAMINE MODIFICATION OF METAL OXIDE SEMICONDUCTORS, METHOD FOR ATTACHING BIOLOGICAL MOLECULES TO SEMICONDUCTORS

CONTRACTUAL ORIGIN OF THE INVENTION

The United States Government has rights in this invention pursuant to Contract Number W-31-109-ENG-38 between the United States Government and Argonne National Laboratory.

BACKGROUND OF THE INVENTION

1. Field of the Invention

This invention relates to a method for attaching and detecting the attachment of biological molecules to semiconductors, and more particularly, the invention relates to a method for attaching biologically active molecules to nanoparticle-size metal oxide semi-conductors.

2. Background of the Invention

Detection of target molecules in an unknown mixture finds a variety of applications. A few of these applications include genome sequencing, forensics, assays, and drug affinity studies.

Typical detection techniques involve the use of fluorescence tags. Such tags are first attached to moieties (having known affinities to target molecules), to create a construct. The construct is then combined with materials in a search for the target molecules suspected of residing in those materials.

A myriad of problems exist with the use of fluorescence molecules in detection schemes. For example, the tags tend to fluoresce at a wide wavelength band and therefore obliterate the "fingerprint" of other concomitantly used fluorescent tags.

Also, fluorescence moieties are short-lived, particularly at wavelengths required to induce fluorescence. As such, exposure times to the wavelengths must often be minimized. Strict ambient conditions also are required to forestall eventual tag denigration.

Efforts have been made to eliminate fluorescence tag usage in detection processes. For example, U.S. Pat. No. 5,990,479 awarded to Weiss et al on Nov. 23, 1999, supplants fluorescence moieties with semiconductor moieties. The semiconductors are attached to affinity molecules to create a construct which in turn is mixed with material suspected of containing target molecules. Detection is noted when the mixture is subjected to light at wavelengths which cause the semi-conductor in the construct to luminesce.

The '479 patent eliminates many of the drawbacks of some fluorescence systems. For example, each semiconductor imparts luminescence at narrow band wavelengths. This feature allows several semiconductors, each with characteristic emission spectra, to be used simultaneously to detect several different target molecules.

However, state of the art semiconductor detection systems do not provide a means for determining the amount of target moiety detected. Also, detection sensitivities are limited to optical characteristics of the semiconductor.

Notwithstanding the foregoing drawbacks in semiconductor systems, the inventors envision exploiting the phenomenon in those substrates whereby radical intermediates are formed following light induced charge pair formation. Electron Paramagnetic Resonance (EPR) is the prime technique for detecting these formations.

Nanocrystalline metal oxide semiconductor particles that are durable and are not susceptible to photo-degradation, act as miniaturized electrochemical cells and act as stable and efficient artificial photosynthetic systems. However, the recombination kinetics in these systems is very fast, on the order of picoseconds. N. Serpone et al. *J. Phys. Chem.*, 99, 16655 (1995). Unless the charge separation is increased by reaction with adsorbed species, the efficiency of charge separation is very low.

A need exists in the art for a detection system based on electronic changes in a foundation substrate. The system should incorporate a means to modify the charge separation tendencies of photo-induced ion pairs on the substrates so as to be measurable with existing time-resolved detection systems. This modification would allow chemical reactions to be efficiently performed using nanocrystalline materials. The system should also serve as a detector for the existence of moieties that would modify the charge separation fingerprint via electron donation or extraction. The charge separation should be detectable via electronic signals and easily amplified.

SUMMARY OF THE INVENTION

An object of the present invention is to provide a method for detecting molecules that overcomes many of the disadvantages of the prior art.

Another object of the present invention is to provide a method for exploiting the charge separation abilities of semi-conductors to create detectors of molecules. A feature of the invention is the utilization of a bidentate or tridentate modifier molecule as an electron donor or acceptor to the semiconductor. An advantage of the invention is the prolongation of charge separation on the semi-conductor as an indicator of the type of molecule juxtaposed and electrically connected to the semi-conductor particle.

Yet another object of the present invention is to provide a method for selective binding and modifying of molecules in vivo or in vitro. A feature of the method is that a nanocrystalline-biological construct, capable of photochemical response, and capable of simultaneously carrying a number of biologically active molecules, can bypass biological membranes via standard delivery methods. An advantage of the method is that oxidative damage, produced by positive charge centers (resulting in the formation of oxygen centered radicals covalently linked to surface semiconductor atoms), facilitates the cleaving and recombination of particle-attached molecules to reactive sites. Another advantage is that a collection of biologically active molecules can be delivered to, and therefore co-localized at, the reactive sites to facilitate simultaneous action of the delivered biomolecules.

Still another object of the present invention is to provide a molecule detection system which also quantifies the amount of target molecule present. A feature of the present invention is the utilization of a nanocrystalline foundation material capable of binding a plurality of linker moieties, whereby the moieties link the material to the target molecule. An advantage of the invention is that the detector construct facilitates selective adsorption and selective chemical reactions at the surface of the material.

Briefly, the invention provides for a method for detecting molecules, the method comprising determining the electronic status of a semi-conductor; establishing electronic communication between the molecules and the semiconductor; subjecting the semi-conductor to energy influx; and redetermining the electronic status of the semi-conductor.

Also provided is a method for detecting biological molecules, the method comprising supplying a semiconductor having a first energy level and a second energy level and whereby the first energy level corresponds to a first optical characteristic of the semi-conductor; establishing electrical contact between the semi-conductor and the molecules; causing electrons to move from the molecules to the second energy level; and monitoring any change in the first optical characteristic.

Also provided is a method for detecting target moieties in situ, the method comprising binding biological material to nanocrystalline semiconductor particles, wherein the material has an affinity to the target moiety; facilitating entry of the bound material into an organelle; and subjecting the semiconductor to radiation sufficient to produce a charge pair separation on the semiconductor's surface.

BRIEF DESCRIPTION OF THE DRAWING

Other objects, features, and advantages of the present invention will become apparent from the following description and the accompanying drawings, wherein.

DETAILED DESCRIPTION OF THE INVENTION

The invention relates to multiple biological use of nanocrystalline semiconductors bound to oligonucleotides, DNA segments and peptides for selective binding and hybridization, photophysical and photochemical DNA and protein chemistry in vitro and in vivo. In one specific example, surface modification of nanocrystalline metal oxide particles with ortho substituted hydroxylated aromatic ligands was found to result in bidentate coordination of surface Ti atoms. Due to specific bindings of surface modifiers, the optical properties of the small titania particles change with absorption shifting to the red, compared to unmodified nanocrystallites (for salicylate 0.8 eV, ascorbate 1.6 eV and dopamine 1.85 eV). The binding is exclusively characteristic of small particle colloids in the nanocrystalline domain and was found to be a consequence of adsorption induced reconstruction of the nanoparticle surface.

A salient feature of the invention is the enhanced charge separation and improved optical properties of nanocrystalline semi-conductors that involve photoinduced interfacial electron transfer from surface modifiers into one or more regions of the semi-conductors. The charge pairs are instantaneously separated into two phases, the holes on the donating organic modifier and the donated electrons in either the conduction band or valence band of the semi-conductor.

Surface modifications of the nanocrystalline particle with bidentate ortho-substituted hydroxylated electron donating ligands, combined with laser excitation of the modified particle, causes a protracted electron decoupling from surface moieties resulting in a correlated radical pair electron spin mechanism, reminiscent of the ion cascade seen in optimized natural photosynthetic systems.

The invention exploits the electrochemical cell characteristics of particulate semiconductors. Inasmuch as the detection system is based on charge separation, the presence or absence of such charge separation (indicative of the presence of certain target moieties), can be measured electronically. Furthermore, the electronic signals generated by this separation can be amplified, thereby providing a sensitivity of the detection system that is superior to those systems relying on typical.fluorescence protocols.

It should be noted that a myriad of semiconductors can be utilized to produce the detection device. Titania is depicted herein merely for the sake of illustration.

Figure 1:
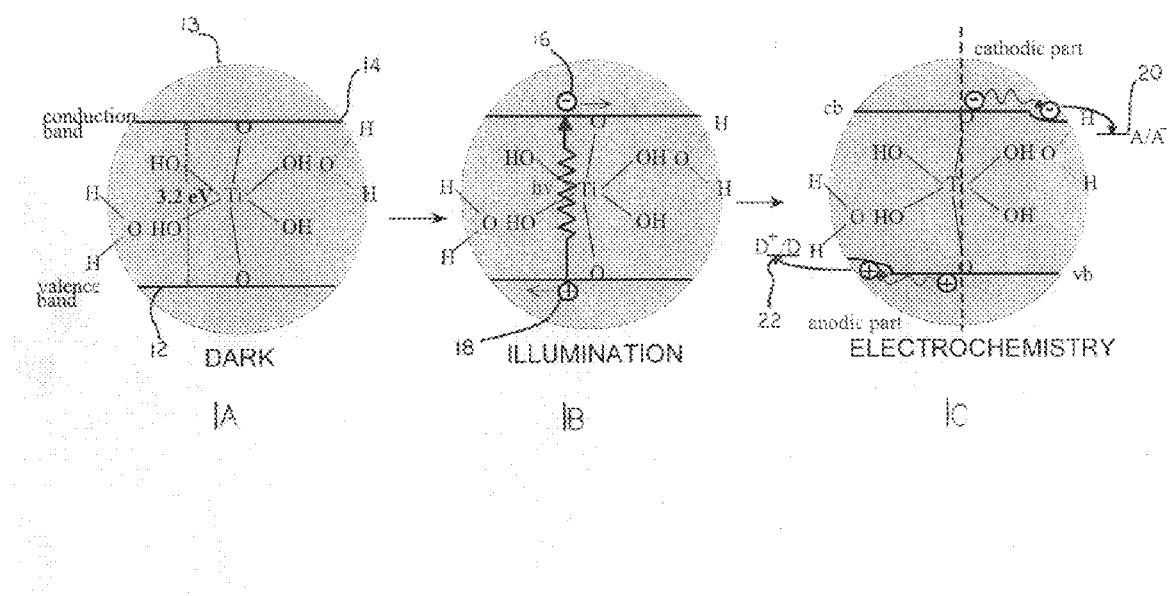
FIG. 1 is a schematic diagram of the electronic state of semiconductor particles, in accordance with features of the present invention.

As depicted in FIG. 1A, semiconductors have an energy band structure characterized by a gap between the highest occupied energy level 12 (or valence band) and the lowest unoccupied energy level 14 (or conduction band). In the case of titanium oxide, the gap is 3.2 eV. A single semiconductor particle 13 is depicted.

A disturbance in the energy level of the electrons in the valence band in the semiconductor is induced via illumination (FIG. 1B). Upon illumination with photons having energy greater than the band gap, an electron 16 is excited to the conduction band 14 while in the valence band 12 a positive 18 hole is created.

As depicted in FIG. 1C, the electrons and holes generated via the illumination can separate and diffuse to the surface of the semiconductor. This surface diffusion allows the diffused electrons and holes to react with redox couples to undergo reduction reactions 20 and oxidation reactions 22, respectively.

Figure 5:
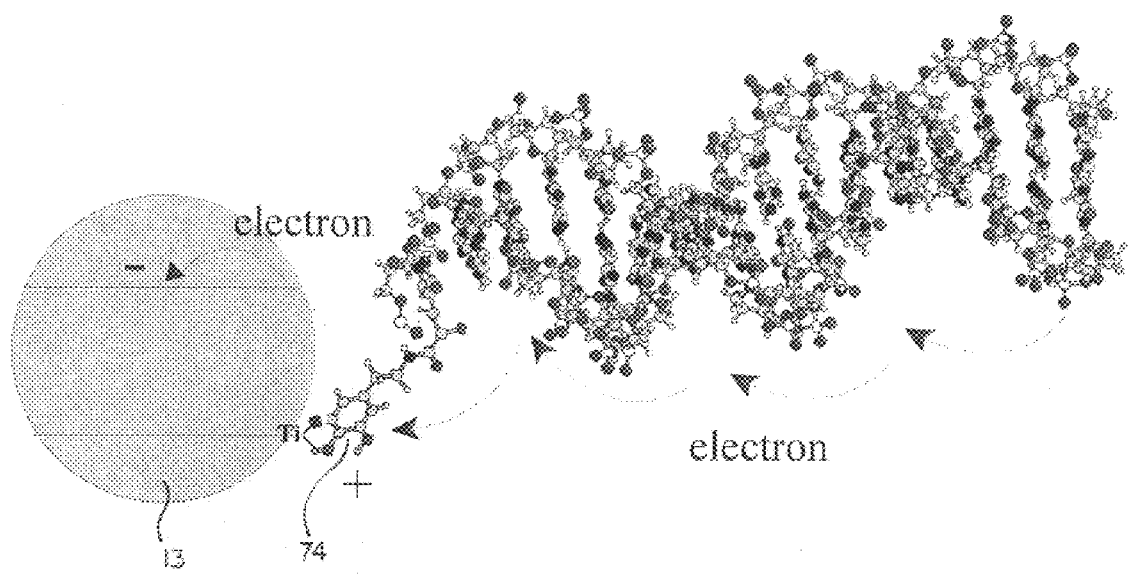
FIG. 5 is a schematic diagram showing an electron cascade from a molecule toward the modified surface of a semi-conductor particle, in accordance with features of the present invention.

A cornerstone of the invention is the juxtaposition of redox moieties to the particle. Without the utilization of such close proximity electrophillic and nucleophillic moieties, rapid recombination of the photogenerated charge pairs (i.e. the electron 16 in the conductance band and the "hole" 18 in the valence band) occurs, particularly since the pairs are located on the same particle. As such, the inventors have devised machinery to convert light energy into chemical energy via a sequential electron transfer process whereby a series of electron trapping sites are utilized. The machinery serves to facilitate long distance charge separation by blocking the surface states of titania. This enhances the kinetics of desired reactions. For example, with certain molecules attached to the semiconductor particle so as to modify the surface of the particle, electrons can move from those molecules to either the conduction band 14, the valence 12, or both to fill in "holes" created during the excitation phase (FIG. 1B) of the process. When additional molecules are attached to these modifiers (for example when DNA is attached to the modifier Dopamine 74, as depicted in FIG. 5) the cascade may be protracted. When electron extraction molecules are attached to the DNA (i.e. certain proteins), the cascade maybe blocked, resulting in no absorbance shift or change in electronic state on the surface of the particle 13.

Figure 2:
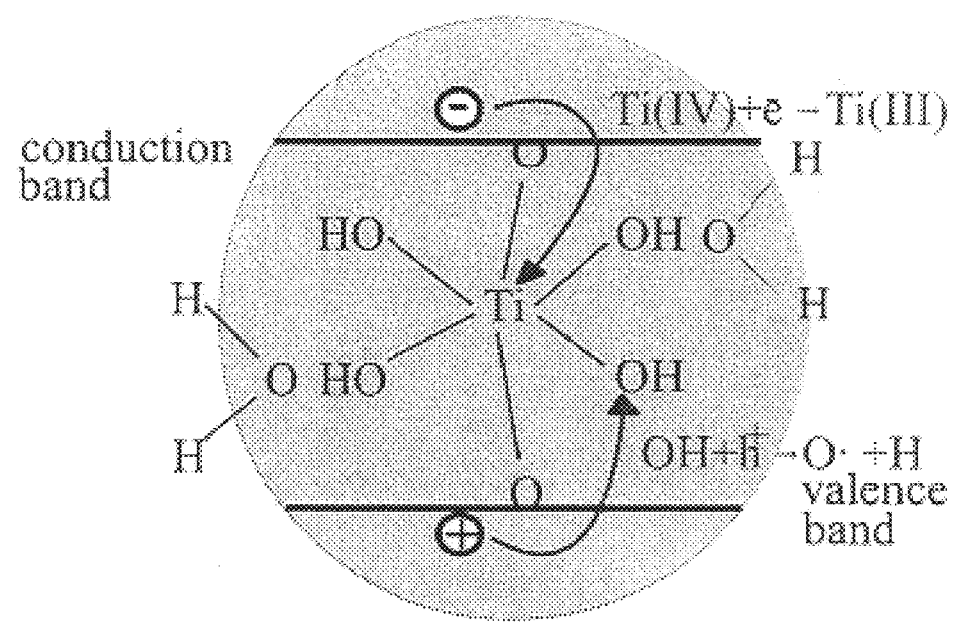
FIG. 2 is a schematic diagram of the fate of photogenerated charge pairs on particulate semi-conductors, in accordance with features of the present invention.

Electron Paramagnetic Resonance (EPR) has shown that electrons which have been energized to the conduction band, are trapped as reduced metal centers; in the case of $TiO_2$ the electrons facilitate reduction of Ti (IV) to Ti (III). Concomitantly, the holes left in the valence band are trapped as oxygen centered radicals covalently linked to surface titanium atoms. A schematic diagram of this phenomenon is provided as FIG. 2.

Figure 3:
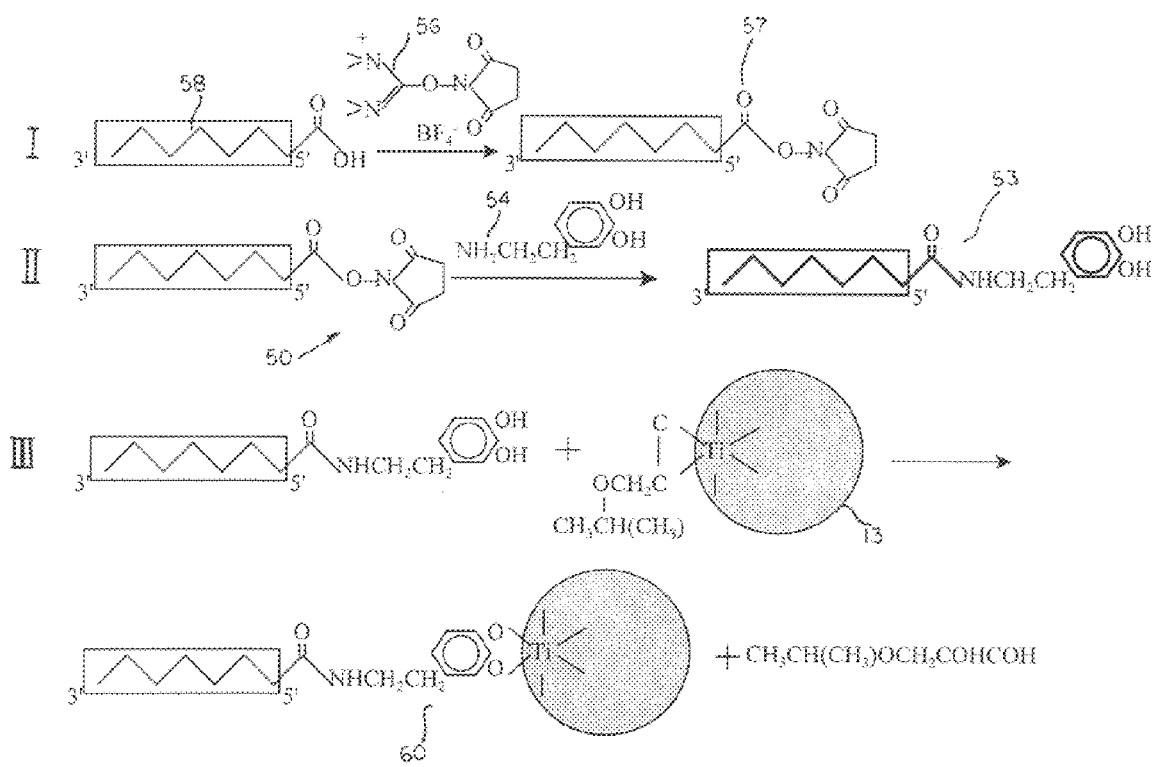
FIG. 3 is a reaction sequence depicting the formation of the invented semi-conductor-biological molecule construct, in accordance with features of the present invention.

A particle-biological molecule construct has been invented, and is the product of an electrophilic reaction between the carboxylic terminus of oligonucleotide and amino-containing electrophilic reagents, the reaction depicted generally as numeral 50 in FIG. 3. In the illustrated embodiment, a semiconductor particle (preferably one having octahedral structure, such as $TiO_2$) 13 is bound to oligonucleotide(s) 58 via a charge-transfer intermediary. This is accomplished by a series of electrophilic and nucleophillic substitutions.

In a first step, depicted as Roman Numeral I in FIG. 3, the oligonucleotide 58 is modified at its carboxylic terminus to contain an ester-moiety. First, the carboxyl terminus is transformed into a succinimide intermediate via extraction of the hydroxyl moiety. Then, in a nucleophillic substitution, the succinimide group is expelled and its place taken by a basic amino group 56 (a suitable amino group found on N-hydroxy-succinimide, as shown) to form an oligo nucleotide with an ester terminus 57.

The ester terminus reacts with one or a plurality of bidentate or tridentate modifiers 54 in reaction sequence II of FIG. 3, to arrive at the oligo-bidentate construct 53 or constructs. As depicted in sequence III, the construct 53 then contacts a nanocrystalline particle 13 of suitable geometry to form the particle-modifier-oligo construct 60. Alternatively, the modifier 54 can already be attached to the particle prior to joining with the oligo-ester terminus 57.)

One suitable class of modifiers are the 1,2 dihydroxyl phenyls, an exemplary species being dopamine. Generally, when oligonucleotides or PNAs are to be ultimately connected to the nanocrystalline particles, the intermediate modifier particles contain amino moieties. The modifiers are strongly coupled to the surface of the nanocrystalline titanium dioxide particles 13.

Additionally, titanium dioxide nanoparticles are bound to proteins, peptide nucleic acids (PNAS) or oligonucleotides. Generally, the particles are coupled to bidentate modified 1,2 dihydroxyl benzoic acids When proteins ultimately are to be complexed with the particles via an intermediate N-hydroxy-succinimide ester in a similar reaction sequence as that depicted in FIG. 3.

The remaining particle surface is protected to prevent undesirable reactions of hydroxyl groups at the titanium surface with carboxyl and phosphordiester groups on the oligo. An exemplary means for protecting the surface is a layer of glycidyl isopropyl ether on the semi-conductor's surface. Generally, any material which removes or otherwise blocks hydroxyl moieties on the titania surface from reacting with target molecules is suitable. In the case of the glycidyl isopropyl ether, a layer approximating 5 angstroms (Å) in thickness is suitable.

Figure 4:
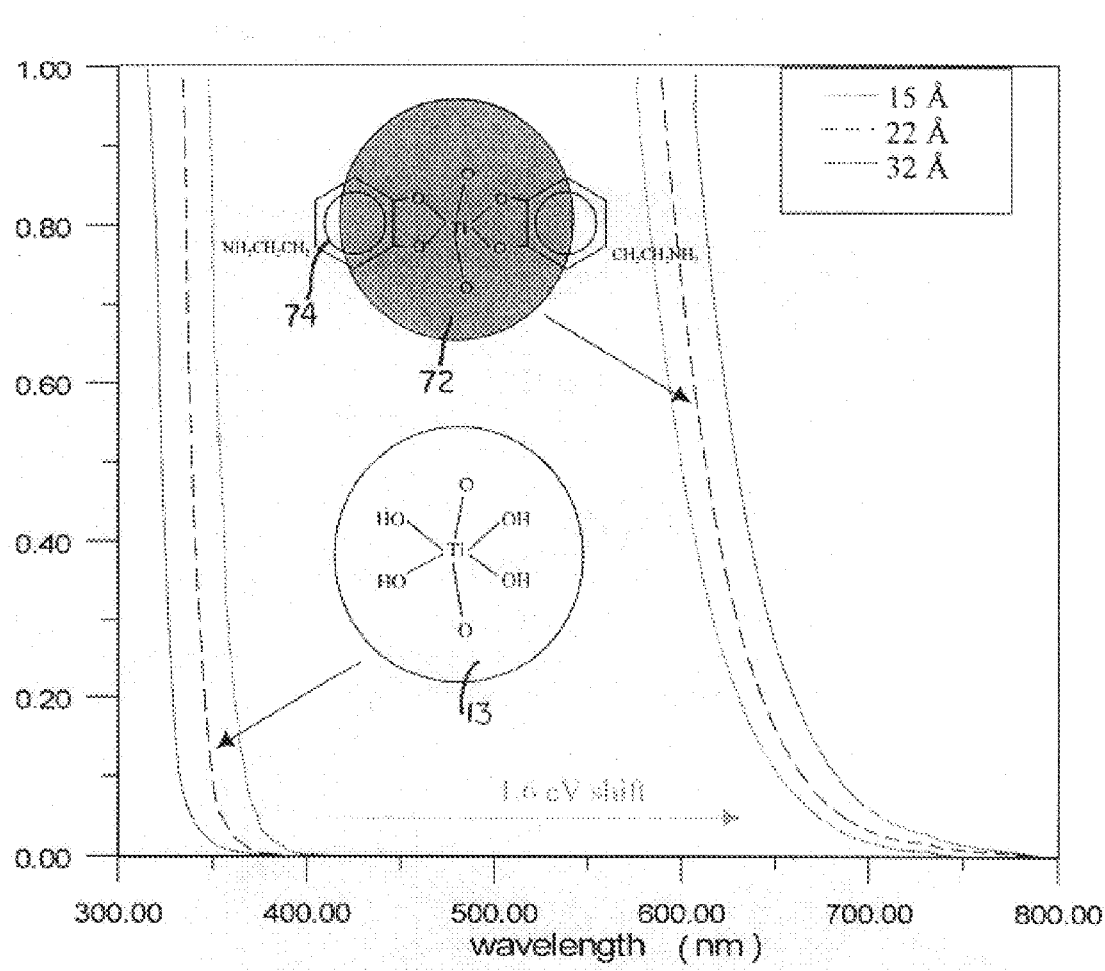
FIG. 4 is a graph showing a red-shift of modified nanocrystalline particles, in accordance with features of the present invention.

A salient feature of the invented process is the observation of a red-shift which results when certain modifiers are present on nano-sized semi-conductor particles. Specifically, and as depicted in FIG. 4, unmodified $TiO_2$ particles 13 exhibit absorbency at approximately 400 nm. However, when modifier moieties (such as dopamine, 74) are attached to the particle, the resulting construct 72 exhibits a shift in absorbency to a longer wavelength of approximately 600 nm.

The absorption in the red region reflects the presence of the excess electrons in the excited state of $TiO_2$ and is due to the absorption of localized and delocalized electrons (Ti(III)) in $TiO_2$. The shape of this part of the spectrum in which the absorption spectrum of excess electrons shows characteristic increased absorption with longer wavelengths is consistent either with free carrier absorption and/or absorption to shallow defect sites on interstitial Ti atoms.

Degree of upshift serves as an indicator as to how much of an electron donor molecule is present and electronically communicating with the semi-conductor surface modifying agent, or the particle surface itself. For example, the inventors have found that a four-member ring results in less of a shift than a five-member electron donor. This is primarily due to the easier ability for resonance electrons to leave the larger ring structure and cascade toward the particle surface. A schematic depiction of such a cascading phenomenon is illustrated in FIG. 5 wherein DNA is shown facilitating sequential electron transfer to the surface of the particle.

Component Detail

The illustrations and protocol provided herein utilize titanium oxide as the semi-conductor particle, solely for illustrative purposes. A myriad of metal oxides are suitable particle candidates. As such, aside from the titanium dioxide, other nanocrystalline (1–20 nm) octahedral metal oxides such as $VO_2$, $ZrO_2$, $Fe_3O_4$, $MnO_2$, NiO and CuO could be used.

As mentioned supra, it is preferable that the semi-conductors utilized be of an octahedral structure when dopamine or some similar dihydroxyl phenyl molecule is utilized as a surface modifier. Octahedral structure of the foundation nanocrystalline material is necessary in the illustrated construct so as to facilitate relatively unhindered coupling with the bond angles provided by the dopamine bridging group.

Generally though, any nanocrystalline material and modifying surface molecule, which when combined maintain their respective surface geometries, are suitable components of a redox pair.

Regarding semi-conductor surface modifiers, a myriad of multifunctional ligands are suitable. Such ligands should have groups with varying donor acceptor character, selective binding of reactants, and for the binding to the surface of the semi-conductor particle. The following is a list of suitable bidentate and tridentate functional moieties:

| | | |
|---|---|---|
| mercapto (SH) | amino (—$NH_2$) | α-hydroxyl (—OH—OH) |
| carboxyl (—COOH) | phosphono (P(O)(OH)$_2$) | |

These moieties can be presented in different combinations, relative positions and hydrocarbon chain lengths. As noted supra, the choice of modifier molecules also will be dependant upon the bond angle geometry of the foundation nanocrystalline semiconductor material.

In one embodiment, the invention provides working solutions of modified semiconductor nanocrystallites (1–20 nm) which are modified with specific moieties. The modifier, such as oligonucleotide, provides both hole scavenging (photochemical and photophysical response) and selective binding functions in vitro and in vivo. Inasmuch as the oligonucleotide-dopamine-nanocrystalline construct is unobtrusive (1–20 nm when TiO2 is utilized), its insertion into biological systems (in vivo and in vitro) is not problematic.

Transfection Detail

Transfection of eukaryotic cells with nanoparticle-oligonucleotide complexes were performed. Two different human cell lines (HL60 and HeLa) were transfected with six different oligonucleotides (4S, 2S, r18RS, r28RS, MIT1, and MIT2) bound to nanoparticles, wherein the oligonucleotides have the following base sequences:

| 2S | 5' carboxy dT-GCATGCATGGATGGA |
|---|---|
| 4S | 5' carboxy dT-GGATGGATGGATGGA |
| MIT1-S5T | 5' carboxy dT-CCACTTTCCACACAG |
| MIT2-S5T | 5' carboxy dT-AGACCAAGAGCCTTC |
| R18S-S5T | 5' carboxy dT-TTCCTTGGATGTGGT |
| R28S-S5T | 5' carboxy dT-CAGGATTCCCTCAGT. |

Transfection was done with QIAGEN SuperFect Transfection Reagent (as follows (basically according to the manufacturer's instructions):

For HeLa cells, 200,000 cells each were plated on 60 mm 2 dishes a day before transfection. For HL60 cells 2,000,000 cells were plated on 60 mm² dishes on the day of transfection in 4 ml of cell growth medium (DMEM for HeLa and RPMI160 for HL60 cells) with 10% fetal calf serum and incubated at 37° C. with 5% $CO_2$. HeLa cells are seeded a day in advance at a density of $2 \times 10^5$ and allowed to grow over night to a density of $2 \times 10^6$. HL60 cells, on the other hand, are used immediately, and seeded at $2 \times 10^6$ density.

Oligonucleotide-nanoparticle suspensions had 2 to 8 $\mu$M concentrations. Between 2 and 50 $\mu$l of solution was mixed with 20 $\mu$l of SuperFect Reagent and some serum free medium up to the final volume of 150 $\mu$l.

Mixtures were incubated at room temperature for 10 minutes, mixed with 1 ml of cell growth medium with serum and then applied on cells drop-wise. Cells were incubated 2 to 8 hours at 37° C. and 5% $CO_2$.

Cells were collected (HeLa cells were detached from the plate by trypsinization) by centrifugation of 10 minutes at 700 g, resuspended in Phosphate Buffered Saline (PBS), and re-precipitated. Finally, cells were resuspended in 40 $\mu$l of PBS and applied on EM grids. Cells prepared like this were dried by 10 min incubation in ethanol (100%) and Ti was detected by fluorescent microprobe at the Advanced Photon Source 2ID-E beamline at Argonne National Laboratory, Argonne, Ill.

The following applications can be envisioned:
Sensors of DNA-protein
Complex Formation Detail In this instance, the titania-dopamine-oligo construct is attached to DNA which is capable of hole scavenging (electron donating). Upon illumination of the construct, electrons are transferred from DNA to the valence band of $TiO_2$ to neutralize the positive holes originally produced from the photogenerated electrons which resided there (and which now reside in the conductance band of the titania). This changes the optical properties of $TiO_2$ and a blue color (absorption at ~600 nm) appears. Subsequent addition of a source of conductive metal ions such as silver, gold or copper ions will reduce metal ions to form conductive elemental metal. Upon DNA binding to electron-withdrawing proteins, the electron transfer does not occur and the change of the optical properties does not occur. As such, a lack of color change or lack of alteration of the electronic state of the titania particle indicates that an electrophillic moiety is attached to the titania-dopamine construct.

In another embodiment, the invention is carried out by applying free standing DNA and PNA oligo and peptide modified (1–20 nm) semiconductor nanocrystallites such as $TiO_2$ in solution. The modifier such as DNA or PNA oligo provides both selective hybridizing and hole scavenging functions (photochemical response) in vivo. The particles will bypass cell, nuclear, or mitochondrial membranes using standard delivery methods combined with attachment to peptides that facilitate entry into cells or their compartments. The following applications can be envisioned:

Gene Replacement

Particles are attached to peptides that facilitate entry into cells (and/or their compartments), and then to both a DNA strand with a copy of normal gene and a single stranded DNA or PNA oligo of sequence complementary to the host sequence where the excision is needed. Cutting will be achieved by oxidative damage produced by photogenerated holes at the $TiO_2$ surface. The resulting DNA break will facilitate recombination which will exchange the mutant/abnormal gene of the host with the introduced normal gene bound to the $TiO_2$ particle.

Gene Ablation

Particles are attached to peptides that facilitate entry into cells (and/or subcellular compartments), and then to a DNA strand with a single stranded DNA or PNA oligo of sequence complementary to the host sequence which is to be excised. Cleavage/excision are achieved by oxidative damage produced by photogenerated holes at the TiO2 surface. Resulting DNA breaks within amplified or abnormal genes will facilitate recombination which will excise excess copies or mutant copies of the gene.

Suicide Gene
Implantation Detail

Particles are attached to peptides that facilitate entry into cells (and/or their subcellular compartments), and then to both a DNA strand with a copy of a cellular suicide gene and a single stranded DNA or PNA oligo of sequence complementary to the host sequence of a promoter of a gene involved in proliferation or some other essential cellular function which is to be replaced to permit expression of the suicide gene. Excision will be achieved by oxidative damage produced by photogenerated holes at the TiO2 surface. The resulting DNA break will facilitate recombination which will exchange the host proliferative (or some other expressed) gene with the introduced suicide gene bound to the TiO2 particle.

In Vivo
Manipulation Detail

In another embodiment the invention is carried out by applying free standing oligonucleotide, PNA oligo, peptide or protein modified (1–20 nm) semiconductor nanocrystallites such as $TiO_2$ in solution. The modifier such as oligonucleotide, PNA or protein provide selective binding and hybridizing in vivo. The particles will bypass cell or subcellular membranes using standard delivery methods combined with attachment to peptides that facilitate entry into cells/subcellular compartments. The following applications can be envisioned:

Nanocrystalline particles are attached to a test DNA strand and also modified, if necessary, with a peptide that is responsible for "homing" into the nucleus and a peptide that facilitates entry into cells. After incubation sufficient for nuclear proteins to bind DNA, methylation of DNA is achieved using external agents. Particles are isolated after cell lysis and DNA is purified by hybridization to a solid support (column) and footprints are developed.

Nanoprotein
Torpedoes

A battery of specific proteins that carry out DNA repair are attached to nanocrystalline particle and delivered to the cells that require repair (such as those damaged by chemotherapy, radiation exposure, etc. or those from people with repair deficiencies). Additionally particles are attached to peptides that facilitate entry into cells/subcellular compartments.

Intracellular Drug
Delivery Detail

Drug molecules can be attached to particles together with antibodies or other molecules that recognize specific cell types and peptides that facilitate entry into cells/subcellular compartments for targeted drug delivery.

In situ PCR
Detail

PCR primer(s) and subsequent nested primer(s) can be attached to particles that can help visualize the genomic/chromosomal location of a PCR reaction. Particles can also have attached antigen that can serve for subsequent isolation of PCR products via Ag-Ab reactions. Particles are also attached to peptides that facilitate their entry into cells/subcellular compartments.

In Vitro
Manipulation Detail

In another embodiment the invention is carried out by applying DNA and PNA oligo modified (1–20 nm) semiconductor nanocrystalline films, such as $TiO_2$ thin films, on glass mesh or some other support. The modifier (for example, an oligonucleotide) provides both hole scavenging (photochemical and photophysical response) and selective hybridization binding functions in vitro. Following application can be envisioned:

Purification of Sequence Specific DNA
Binding Proteins or Proteins that Repair DNA Nanocrystalline titania films on glass mesh or other supports modified with DNA of defined sequence or with specific base or nucleotide damage will selectively bind proteins that recognize the sequence of DNA or recognize damaged DNA.

Purification of RNA-Binding Proteins Essential
In Splicing, RNA Processing, or RNA Stability Nanocrystalline titania films on glass mesh or other supports modified with DNA or RNA of defined sequence will selectively bind proteins that recognize the sequence of RNA and participate in splicing, RNA processing, or RNA stability.

Recyclable" Template for Transcription Coupled
Translation or Transcription Coupled Repair Nanocrystalline titania films on glass mesh or other supports modified with DNA of defined sequence can serve as templates for in vitro transcription and translation. Similarly, nanocrystalline titania films or glass mesh of other supports modified with DNA that is damaged can serve as templates for in vitro repair of DNA or of transcription-coupled repair.

DNA Hybridization
Chip Detail

Oligonucleotides can be attached to titania films or other supports and their hybridization with probes can be detected via an electric signal created by an electron and hole migration in a miniature photoelectrochemical cell. The cell is created by immobilization of oligonucleotide modified TiO2 particles on conductive supports. Each of the particles modified with specific sequence would be connected into a separate circuit with a platinum or glassy carbon electrode immersed into an electrolyte containing easily oxidizable redox couple such as absorbate or iodine. Upon illumination holes created in the valence band of TiO2 will migrate to DNA chain provided that it is double stranded and an electron will be left on TiO2 and driven to platinum or glassy carbon cathode. Double stranded DNA is made only upon hybridization with probe. Selectivity (stringency) of hybridization can be adjusted to the thermal stability of each individual oligonucleotide and selectively probed at different washing temperature shifts. A very important feature of this type of "chip" is that it can be used both for mutation detection and monitoring of cDNA populations (gene expression).

DNA-Protein Interaction DNA Chip

Double stranded oligonucleotides can be attached to titania films or other supports in the above-mentioned photoelectrochemical cell. In this case all the leads will carry electrical impulses upon illumination. Upon coupling of double-stranded oligonucleotide with sequence specific proteins charge separation will be prevented. Therefore the lack of electrical signal would indicate DNA protein interaction.

Particle-Molecule
Preparation Detail

All the chemicals were reagent grade and used without further purification (Sigma, Aldrich or Baker). Triply distilled water was used. The pH was adjusted to pH 3.5 with NaOH or HCl. Oxygen was removed by bubbling with argon or nitrogen. Colloidal $TiO_2$ was prepared by dropwise addition of titanium(IV) chloride to cooled water. The temperature and rate of component mixing of reactants were controlled by an apparatus developed for automatic colloid preparation. One such apparatus as disclosed in M. C. Thurnauer, *Acta Scandinavica* 51, pp. 610, (1997), and incorporated herein by reference.

The concentration of $TiO_2$ (0.1–0.6 M) was determined from the concentration of the peroxide complex obtained after dissolving the colloid in concentrated $H_2SO_4$, as described in Thompson, *Inorganic Chem.*, 23, p 1794, (1989) and incorporated herein by reference. Surface modification of $TiO_2$ with ascorbate resulted in the charge transfer complex with optical properties which were described in T. Rajh, *J. Phys. Chem. B.*, 103, pp 3513, (1999), and also incorporated herein by reference. Dopamine was also used for surface modification of $TiO_2$ but the onset of absorption in this system was further shifted to 810 nm.

The following specific protocol was utilized:

Dopamine was added into $TiO_2$ colloidal solutions at 8<pH<2.5. Immediate development of red color indicates instantaneous formation of the charge transfer complex between dopamine and $TiO_2$. The amount of adsorbed dopamine can be determined by measuring absorption at 440 nm, at extinction coefficient of $3.3 \times 10^3$ $M^{-1}cm^{-1}$, absorption at 520 nm at an extinction coefficient of $1.1 \times 10^3$ $M^{-1}cm^{-1}$, or in higher concentrations with absorption at 570 nm with an extinction coefficient of $1 \times 10^2$ $M^{-1}cm^{-1}$.

The Dopamine/$TiO_2$ complex (i.e., the resulting construct) is extremely stabile and cannot be removed by dialysis. Stability of the construct is larger than the stability of a complexes between $TiO_2$ and glycidil, glycidil isopropyl ether, amino propyl silane or phenyl silane. At alkaline pH>8.5 dopamine modifier is readily removed from the $TiO_2$ surface.

Coupling of dopamine end-labeled oligonucleotides to $TiO_2$ particles should be performed at pH 6.5 and in 10–40 mM phosphate buffer. $TiO_2$ colloids prepared at pH 3.5 were diluted to 0.015M and 50 ml was mixed with 100 μl of glycidil isopropyl ether. With vigorous mixing, 1 ml of 0.2 M LiOH was rapidly injected into the $TiO_2$ solution until a pH of 9.5 was reached, per the protocol disclosed in Rajh, T. *Langmuir*, 8, 1265 (1992). The solution is dialyzed against 10–40 mM phosphate buffer until it reaches pH 6.5.

Binding end-labeled DNA with dopamine to $TiO_2$ results in the same optical changes and therefore could be quantified in the same manner.

Transient absorption measurements were performed at room temperature on the system previously described in Greenfield. S. R., *Opt. Lett.* 20, p 1394 (1995), and incorporated herein by reference.

EPR: The direct detection time-resolved X-band EPR experiments were collected on a Bruker ESP300E spectrometer equipped with a Varian cavity and a variable temperature cryostat (Air Products, LTD) cooled to helium temperatures. The transient signal at 1 μs after laser flash and a dark background signal between the laser pulses were collected with Stanford Research System gate integrators and boxcar averagers.

Samples were excited using a nanosecond OPO laser system (Opotek Inc.). Light modulation-field modulation X-band EPR experiments were collected on a Varian E-9 EPR spectrometer equipped with a Varian cavity and a variable temperature cryostat (Oxford) cooled at helium temperatures. The light modulation experiments were carried out as described in L. L. Feezel et al. *Biochim Biophy. Acta* 974 p. 149 (1989). Xe 300 W lamp (Orion Corp) pulsed at 500 Hz was used as an excitation source.

Samples were checked for background EPR signals before irradiation. The g-factors were calibrated by comparison to a $Mn^{2+}$ standard in SrO matrix (g=2.0012±0.0002), as described in J. Rosenthal, et al., *Rev. Sci. Inst.*, 37, 381 (1966) and incorporated herein by reference.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for detecting target molecules, the method comprising:
   a) determining the electronic status of a semiconductor;
   b) establishing electronic communication between the target molecules and the semiconductor;
   c) subjecting the semiconductor to energy influx sufficient to produce a charge pair separation on the semiconductor's surface, thereby generating an electronic signal;
   d) prolonging the charge separation via a semiconductor surface-modifying molecule;
   e) redetermining the electronic status of the semiconductor by amplifying the electronic signal.

2. The method as recited in claim 1, wherein the energy level is determined optically.

3. The method as recited in claim 1, wherein the energy level is determined electrically.

4. The method as recited in claim 1, wherein the semiconductors are metal oxides selected from the group consisting of $TiO_2$, $VO_2$, $ZrO_2$, $Fe_3O_4$, $MnO_2$, NiO, CuO, and combinations thereof.

5. The method as recited in claim 1 wherein bidentate moieties are positioned intermediate the molecules and the semiconductors.

6. The method as recited in claim 1, wherein the semiconductor further comprises a valence band and a conductive band, whereby the valence band contains electrons.

7. The method as recited in claim 6, wherein the energy influx induces the electrons to relocate to the conductance band.

8. The method as recited in claim 1 wherein the molecules are electron donators.

9. The method as recited in claim 1 wherein the molecules are electron acceptors.

10. A method for detecting molecules, the method comprising:
    a) determining the electronic status of a semiconductor;
    b) establishing electronic communication between the molecules and the semiconductor;
    c) subjecting the semiconductor to energy influx and;
    d) redetermining the electronic status of the semiconductor; wherein the semiconductor is an octahedral metal oxide.

11. The method as recited in claim 10, wherein the step of redetermining the electronic status further comprises amplifying an electronic signal created when the semiconductor is subjected to energy influx.

12. The method as recited in claim 10 wherein the molecules are electron donators.

13. The method as recited in claim 10 wherein the molecules are electron acceptors.

14. A method for detecting molecules, the method comprising:
    c) determining the electronic status of a semiconductor;
    establishing electronic communication between the molecules and the semiconductor;
    c) subjecting the semiconductor to energy influx; and
    d) redetermining the electronic status of the semiconductor, wherein bidentate moieties are positioned intermediate the molecules and the semiconductor, and wherein the moieties are dihydroxyl phenyls selected from the group consisting of 1,2-dihydroxyl phenylamine, 1,2-dihydroxyl phenyl alanine, 1,2-dihydroxyl benzoic acid, 1,2-dihydroxyl glycine, 1,2-dihydroxyl benzyl amine, and combinations thereof.

15. A method for detecting biological molecules, the method comprising:
    a) supplying a semiconductor having a first energy level and a second energy level and whereby the first energy level corresponds to a first optical characteristic of the semiconductor;
    b) establishing electrical contact between the semiconductor and the molecules;
    c) causing electrons to move from the molecules to the second energy level, wherein a charge separation occurs on the surface of the semiconductor;
    d) using a semiconductor surface-modifying molecule to prolong the charge separation; and
    e) monitoring any change in the first optical characteristic.

16. The method as recited in claim 15, wherein the biological molecule extracts electrons from the semiconductor.

17. The method as recited in claim 15, wherein the biological molecule donates electrons to the semi-conductor.

18. The method as recited in claim 15, wherein a bidentate moiety is intermediate the semi-conductor and the biological molecule.

19. The method as recited in claim 15 wherein a moiety capable of withdrawing electrons from the biological molecule is in electrical communication with the molecule.

20. The method as recited in claim 15 wherein a moiety capable of donating electrons to the biological molecule is in electrical communication with the molecule.

21. The method as recited in claim 15, wherein the semi-conductor is between 1 and 20 nanometers in diameter.

22. The method as recited in claim 15 wherein the step of causing electrons to move results in the formation of an oxidative region on the semiconductor.

23. A method for detecting biological molecules, the method comprising:

a) supplying a semiconductor having a first energy level and a second energy level and whereby the first energy level corresponds to a first optical characteristic of the semiconductor;

b) establishing electrical contact between the semiconductor and the molecules;

c) causing electrons to move from the molecule to the second energy level; and d) monitoring any change in the first optical characteristic, wherein the semiconductor is an octahedral metal oxide.

24. The method as recited in claim 23, wherein the biological molecule extracts electrons from the semiconductor.

25. The method as recited in claim 23, wherein the biological molecule donates electrons to the semiconductor.

26. The method as recited in claim 23, wherein a bidentate moiety is intermediate to the semiconductor and the biological molecule.

27. The method as recited in claim 23, wherein the semiconductor is between 1 and 20 nanometers in diameter.

28. A method for detecting biological molecules, the method comprising:

a) supplying a semiconductor having a first energy level and a second energy level and whereby the first energy level corresponds to a first optical characteristic of the semiconductor;

b) establishing electrical contact between the semiconductor and the molecules;

c) causing electrons to move from the molecule to the second energy level, resulting in the formation of an oxidative region on the semiconductor, wherein the oxidation region facilitates the cleavage of molecules; and d) monitoring any change in the first optical characteristic.

29. A method for detecting target moieties in situ, the method comprising:

a) binding biological material to nanocrystalline semiconductor particles, wherein the material has an affinity to the target moiety;

b) facilitating entry of the bound material into an organelle; and c) subjecting the semiconductor to radiation sufficient to produce a charge pair separation on the semiconductor's surface; and d) using semiconductor surface-modifier molecules to prolong the charge separation.

30. The method as recited in claim 29 wherein the biological material is genetic material.

31. The method as recited in claim 29 wherein the organelle is a nucleus of a cell.

32. The method as recited in claim 29 wherein the charge pair separation is detected via Electron Paramagnetic Resonance.

33. The method as recited in claim 29 wherein the charge separation is detected via an electronic signal.

34. The method as recited in claim 33 wherein the signal can be amplified.

* * * * *

UNITED STATES PATENT AND TRADEMARK OFFICE
CERTIFICATE OF CORRECTION

PATENT NO. : 6,677,606 B1
DATED : January 13, 2004
INVENTOR(S) : Tijiana Rajh et al.

It is certified that error appears in the above-identified patent and that said Letters Patent is hereby corrected as shown below:

Column 12,
Line 17, should read:
-- 14. A method for detecting molecules, the method comprising:
    a) determining the electronic status of a semiconductor;
    b) establishing electronic communication between the molecules and the the semiconductor;
    c) subjecting the semiconductor to energy influx;
    d) redetermining the electronic status of the semiconductor, wherein bidentate moieties are positioned intermediate the molecules and the semiconductor, and wherein the moieties are dihydroxyl phenyls selected from the group consisting of 1,2-dihydroxyl phenylamine, 1,2-dihydroxyl phenylalanine, 1,2-dihydroxyl benzoic acid, 1,2-dihydroxyl glycine, 1,2-dihydroxyl benzyl amine, and combinations thereof. --

Signed and Sealed this

Third Day of August, 2004

JON W. DUDAS
*Acting Director of the United States Patent and Trademark Office*